US00PP09778P

United States Patent [19]

Zaiger et al.

[11] Patent Number: Plant 9,778

[45] Date of Patent: Jan. 7, 1997

[54] PEACH TREE 'STAR-FIRE'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 549,924

[22] Filed: Oct. 30, 1995

[51] Int. Cl.[6] ..... A01H 5/00

[52] U.S. Cl. ..... Plt./43.1

[58] Field of Search ..... Plt./43.1, 43.2

*Primary Examiner*—James R. Feyrer

[57] ABSTRACT

A new and distinct variety of peach tree which has the following combination of desirable features that are outstanding in a new variety:

1. Fruit with large size, good flavor and eating quality.
2. Heavy and regular production of fruit.
3. Fruit with firm flesh, good handling and shipping quality.
4. Fruit with a high degree of attractive red skin color.
5. Vigorous upright growth.
6. Coloring of fruit 6 to 8 days before maturity.

1 Drawing Sheet

ORIGIN OF THE VARIETY

The new variety of peach tree was originated by us in our experimental orchard located near Modesto, Calif., as a first generation cross between two selected seedlings with field identification numbers 47EB362 and 57RA292. The maternal parent, with field identification number 47EB362, originated from a cross between a selected seedling from open pollinated O'Henry Peach (U.S. Plant Pat. No. 2,964) seed and a selected seedling from the cross of Sam Houston Peach (non-patent) with May Grand Nectarine (U.S. Plant Pat. No. (2,794). The paternal parent, with field identification number 57RA292, originated from a cross between Amparo Peach (U.S. Plant Pat. No. 6,472) and a seedling selection which originated from a cross between a peach of unknown parentage and June Lady Peach (U.S. Plant Pat. No. 3,022). A large group of these first generation seedlings were grown and maintained by us and gave many and varying characteristics. One such seedling, which is the present variety, being especially desirable with respect to its fruit, was selected for asexual reproduction and commercialization.

ASEXUAL REPRODUCTION OF THE VARIETY

The present new variety of peach tree was asexually reproduced by budding, as performed by us in our experimental orchard located near Modesto, Calif., which shows that all characteristics of the tree and its fruit are established and transmitted through succeeding propagations and come true to the original tree in all respects.

SUMMARY OF THE VARIETY

The new and distinct variety of peach tree is of large size, has vigorous upright growth and is a productive and regular bearer of large, yellow flesh, semi-freestone fruit with good flavor and eating quality. The fruit is further characterized by having firm flesh, good handling and shipping quality, an attractive red skin color and in comparison to Amparo Peach (U.S. Plant Pat. No. 6,472) which it closely resembles, the new variety is approximately 1 week later in maturity.

PHOTOGRAPH OF THE NEW VARIETY

The accompanying photographic illustration shows typical specimens of the foliage and fruit of the new variety of peach tree. The photographic illustration depicts the upper and lower surface of the leaves, an exterior and sectional view of the fruit, with a fruit divided in the suture plane to reveal flesh coloration, pit cavity and a stone remaining in place. The photographic illustration was taken shortly after the fruit was picked at maturity (firm ripe) and the colors are as nearly true as is reasonably possible in a color representation of this type.

DESCRIPTION OF THE VARIETY

The following is a detailed botanical description of the flowers, foliage and fruit of our new peach variety, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Brown to soot brown (6-E-5) to (6-F-5).

Branches:
- *Size.*—Medium.
- *Texture.*—Smooth to medium rough. Varies with age of growth.
- *Lenticels.*—Medium number. Medium size.
- *Color.*—Light brown to brown (6-E-4) to (6-E-5).

Leaves:
- *Size.*—Large. Average length — 6¾". Average width — 1½".
- *Texture.*—Smooth.
- *Petiole.*—Medium length. Medium thickness.
- *Form.*—Lanceolate. Pointed.
- *Margin.*—Crenate.
- *Glands.*—Reniform. Number varies from 1 to 4. Average number 2. Positioned on base of leaf blade and upper portion of petiole.
- *Color.*—Upper surface — green to deep green (28-F-8) to (29-F-8). Lower surface — light green to green (29-E-5) to (29-E-6).

Flower buds:
- *Size.*—Large.
- *Form.*—Plump.

*Length.*—Medium.

Flowers:

*Size.*—Large — showy.

*Blooming period.*—Date of First Bloom Mar. 2, 1994. Date of Full Bloom Mar. 6, 1994. Varies slightly with climatic conditions.

*Pollen.*—Present — self fertile.

*Color.*—Pink.

*Pistil pubescent.*—Pubescence.

Fruit:

*Maturity when described.*—Firm ripe.

*Date of first picking.*—Jun. 30, 1994.

*Date of last picking.*—Jul. 6, 1994.

*Size.*—Large. Average diameter axially 3". Average transversely in suture plane 3 1/16".

*Form.*—Globose — nearly symmetrical.

*Suture.*—Shallow — extends from base to apex.

*Ventral surface.*—Usually rounded.

*Cavity.*—Rounded to slightly elongated in suture plane. Average depth ½". Average breadth 1".

*Base.*—Retuse.

*Apex.*—Varies from slight pistil point to slight depression.

Flesh:

*Ripens.*—Relatively even.

*Texture.*—Firm.

*Fibers.*—Small — tender.

*Flavor.*—Good — mild, good balance between sugar and acid.

*Eating quality.*—Good.

*Juice.*—Moderate.

*Aroma.*—Moderate.

*Amygdalin.*—Undetected.

*Color.*—Yellow to golden yellow (4-A-4) to (4-A-5). Pit cavity — brownish red to coral red (9-B-4) to (9-B-7). Slight bleeding into flesh around pit cavity — heavier near apex.

Skin:

*Thickness.*—Medium.

*Texture.*—Medium — tenacious to flesh.

*Tendency to crack.*—None.

*Down.*—Moderate amount — short in length.

*Color.*—Ground color — yellow to golden yellow (4-A-4) to (4-A-6). Overspread with red (10-C-8) to (10-D-8).

Stone:

*Type.*—Semi-freestone. Flesh adheres slightly to outer edges of stone — varies with maturity of fruit.

*Size.*—Large. Average length 1¾". Average width 1⅛". Average thickness ¾".

*Base.*—Usually rounded — varies from rounded to straight.

*Apex.*—Acuminate.

*Form.*—Oval to obovate.

*Surface.*—Irregularly furrowed toward apex, pitted toward base. Pits vary from elongated to round.

*Ridges.*—Usually round.

*Sides.*—Varies from unequal to equal, ventral surface thin.

*Tendency to split.*—Very slight.

*Color.*—Reddish brown to brown (9-D-5) to (9-D-7).

Use: Dessert.

*Market.*—Local and long distance.

Keeping Quality: Good.

Shipping Quality: Good.

The new peach tree, its flowers, foliage and fruit may vary in slight detail due to climatic conditions, soil type and cultural practices under which the variety may be grown. The present description is that of the variety grown under the ecological conditions prevailing near Modesto, Calif.

We claim:

1. A new and distinct variety of peach tree, substantially as illustrated and described, which is of large size, vigorous, upright growth, and is a regular and productive bearer of large, firm, yellow flesh, semi-freestone fruit with good flavor and eating quality; the fruit is further characterized by coloring 6 to 8 days before maturity, having a high degree of attractive red skin color, having good handling and shipping quality; and in comparison to Amparo Peach (U.S. Plant Pat. No. 6,472), the fruit is approximately 1 week later in maturity.

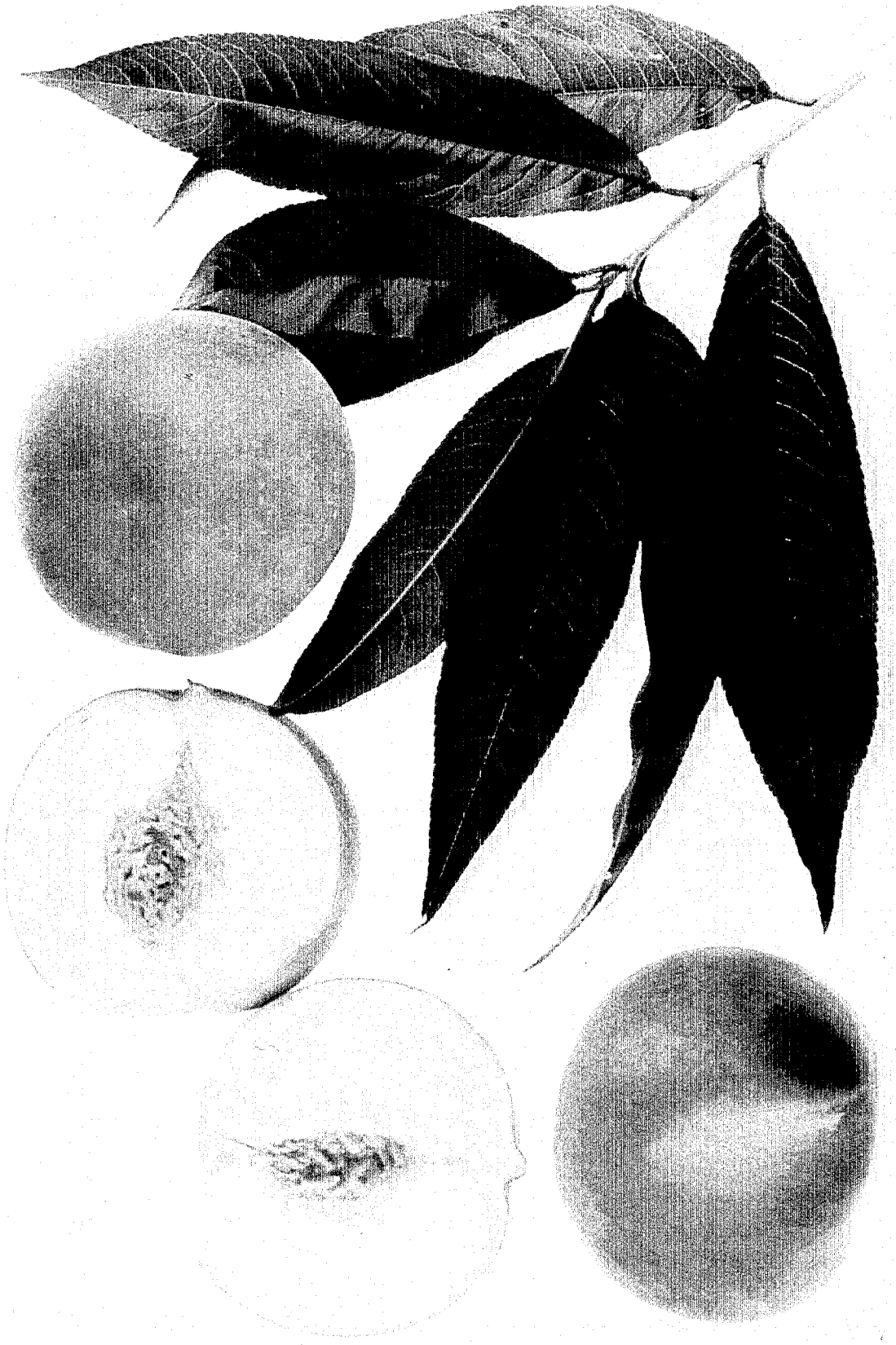

* * * * *